(12) United States Patent
Nishimura et al.

(10) Patent No.: US 8,017,345 B2
(45) Date of Patent: Sep. 13, 2011

(54) DIAGNOSTIC KIT FOR MALIGNANT MELANOMA

(75) Inventors: Yasuharu Nishimura, Kumamoto (JP); Tetsuya Nakatsura, Chiba (JP); Yoshiaki Ikuta, Kumamoto (JP)

(73) Assignee: Kumamoto University, Kumamoto (JP)

( * ) Notice: Subject to any disclaimer, the term of this patent is extended or adjusted under 35 U.S.C. 154(b) by 546 days.

(21) Appl. No.: 11/577,435

(22) PCT Filed: Aug. 9, 2005

(86) PCT No.: PCT/JP2005/014567
§ 371 (c)(1),
(2), (4) Date: Dec. 12, 2008

(87) PCT Pub. No.: WO2006/043362
PCT Pub. Date: Apr. 27, 2006

(65) Prior Publication Data
US 2009/0111095 A1    Apr. 30, 2009

(30) Foreign Application Priority Data

Oct. 19, 2004 (JP) ................................. 2004-303688

(51) Int. Cl.
*G01N 33/53* (2006.01)
*G01N 33/48* (2006.01)
*G01N 33/567* (2006.01)
*C12Q 1/68* (2006.01)

(52) U.S. Cl. ................ 435/7.1; 435/6; 436/64; 436/503

(58) Field of Classification Search ........................ None
See application file for complete search history.

(56) References Cited

U.S. PATENT DOCUMENTS

| 2003/0198970 A1 | 10/2003 | Roberts |
| 2006/0251666 A1 | 11/2006 | Nakatsura et al. |
| 2008/0044818 A1 | 2/2008 | Nishimura et al. |
| 2009/0074800 A1 | 3/2009 | Nakatsura et al. |

FOREIGN PATENT DOCUMENTS

| WO | WO 2004/005883 | * | 1/2004 |
| WO | WO 2005/010213 | * | 2/2005 |

OTHER PUBLICATIONS

Abstract of Kirschner et al (American Journal of Obstetrics and Gynecology, 1996, vol. 174, pp. 1879-1882).*
Nakatsura et al (Clinical Cancer Research, Oct. 1, 2004, vol. 10, pp. 6612-6621).*
Termine JD et al., "Osteonectin, A Bone-Specific Protein Linking Mineral to Collagen", Cell (1981), vol. 26, pp. 99-105.
Mann K et al., "Solubilization of Protein BM-40 from a Basement Membrane Tumor with Chelating Agents and Evidence for Its Identity with Osteonectin and SPARC", FEBS Lett. (1987), vol. 218, pp. 167-172.
Brekken and Sage, "SPARC, A Matricellular Protein: At the Crossroads of Cell-Matrix Communication", Matrix Biol. (2001), vol. 19, pp. 816-827.
Ledda et al., "Suppression of SPARC Expression by Antisense RNA Abrogates the Tumorigenicity of Human Melanoma Cells" Nature Med. (1997), vol. 3, pp. 171-176.
"New Biochemical Experiment 1 (Shin-Seikagaku Jikken Ko-za 1)," Protein I, pp. 389-406, Tokyo Kagaku Dozin Co., Ltd.
U.S. Appl. No. 12/063,165 to Nishimura et al. and entitled "Glycipan-3 (GPC3)-Derived Tumor Rejection Antigenic Peptides Useful for HLA-A2-Positive Patients and Pharmaceutical Comprising the Same."
U.S. Appl. No. 12/304,350 to Nishimura et al. and entitled "SPARC-Derived Tumor Rejection Antigenic Peptides and Medicaments Comprising the Same."
Ikuta, Y. et al., "Highly Sensitive Detection of Melanoma at an Early Stage Based on the Increased Serum Secreted Protein Acidic and Rich in Cysteine and Glycipan-3 Levels", Clinical Cancer Research, Nov. 15, 2005, vol. 11, No. 22, pp. 8079-8088.
Ledda et al., "The Expression of the SPARC is Associated with the Neoplastic Progression of Human Melanoma", The Journal of Investigative Dermatology, Feb. 1997, vol. 108, No. 2, pp. 210-214.
Nakatsura et al., "Identification of Glycipan-3 as a Novel Tumor Marker for Melanoma." Clinical Cancer Research, Oct. 1, 2004, vol. 10, No. 19, pp. 6612-6621.
Bradshaw et al., "SPARC, a matricellular protein that functions in cellular differentiation and tissue response to injury." The Journal of Clinical Investigation, May 2001, vol. 107, No. 9, pp. 1049-1054.
U.S. Appl. No. 10/577,343 (Nishimura et al.), filed Mar. 5, 2007.

* cited by examiner

*Primary Examiner* — Karen Canella
(74) *Attorney, Agent, or Firm* — Greenblum & Bernstein, P.L.C.

(57) ABSTRACT

The object of the present invention is to find out another tumor marker which is useful for early diagnosis of melanoma, and provide a diagnostic kit and diagnostic method for malignant melanoma using such marker. The present invention provides a diagnostic kit for malignant melanoma, which comprises an antibody against SPARC and an antibody against GPC3.

5 Claims, 5 Drawing Sheets a.

b.

DIAGNOSTIC KIT FOR MALIGNANT MELANOMA

TECHNICAL FIELD

The present invention relates to a novel diagnostic kit for malignant melanoma and a diagnostic method for malignant melanoma.

BACKGROUND ART

Melanoma is a type of skin cancer referred to as malignant melanoma. There are various types of skin cancer. Melanoma is the type of skin cancer that has the highest grade of malignancy and thus is very dreaded. Among cells composing skin, melanin-pigment-producing cells are referred to as pigment cells (melanocytes). These cells become cancerous, and melanoma is developed.

The frequency of the occurrence of melanoma in Japan is approximately 1.5 to 2 people per population of 100,000. It is inferred that melanoma annually occurs among approximately 1,500 to 2,000 people in Japan. In the Europe and the United States, the frequency of melanoma incidence is said to be over a dozen people per population of 100,000. The frequency of melanoma incidence in Australia is 20 or more people per population of 100,000, which is said to be the highest in the world. Accordingly, people in Europe, the United States and Australia are interested in melanoma and pay attention to its occurrence. Surprisingly, it has been confirmed that the frequency of the occurrence of melanoma is increasing yearly in both Japan and countries other than Japan. In the latest survey, the annual number of fatalities due to this disease in Japan was as high as around 450 people. Melanoma afflicts people regardless of age. Melanoma occurs more frequently particularly among people aged 40 and up, and occurs most frequently among people aged 60 to 70 and up. Melanoma occurs infrequently among children, but this does not mean that no melanoma occurs among children. Currently, melanoma tends to occur more frequently among young people aged 20 to 30 and up. There are no particular tendencies for melanoma to occur more frequently either in males or females. Melanoma occurs in both males and females. Melanomas in Japanese people are most frequently developed on the soles of the feet (planta pedis). Such melanoma cases account for approximately 30% of all melanoma cases in Japan. Melanomas in Japanese people are characterized in that they are often developed in the toenails and fingernails. Furthermore, similar to melanomas in Western people, melanomas in Japanese people are developed at all skin locations, such as in the trunk, hands, feet, face, head, and the like.

Measurement of serum tumor marker is important not only in melanoma diagnosis, but also in early detection of recurrence in postoperative cases and in determination of therapeutic effects in cases at progressive stages. As tumor markers for melanoma, the usefulness of serum LDH and of 5-S-cysteinyldopa (5-S-CD) has been known to date. In more recent years, S-100β protein and melanoma inhibitory activity (MIA) protein have been reported as more sensitive markers. In Japan, 5-S-CD is broadly used as a tumor marker for melanoma. However, none of these tumor markers yield positive results unless the melanoma is at a highly advanced stage, such as Stage IV. Therefore, it must be said that the usefulness of these tumor markers is limited in terms of melanoma diagnosis and early detection of postoperative recurrence.

The present inventors have previously reported that the glypican-3 (GPC3) is a secretory protein, that GPC3 can be detected in the serum of 40% of hepatocellular carcinoma patients and 40% of melanoma patients using the ELISA method, and that GPC3 is useful as a novel tumor marker for hepatocellular carcinoma (Nakatsura T. et al., Biochem. Biophys. Res. Commun. 306, 16-25 (2003); and Nakatsura, T. et al., Clin. Cancer Res. 10, 6612-6621, 2004).

SPARC (Secreted protein, acidic rich in cysteine, also known as osteonectin or BM-40) was reported in 1981 by Termine et al., as a protein constituting bone. SPARC was also reported in 1987 by Mann et al., as a constituent of the stroma of neoplasm of a basal membrane (Termine J D et al., Cell, 26: 99-105, 981; and Mann K et al., FASEB J 218: 167-172, 1987).

SPARC is an intercellular cement glycoprotein having various functions. The major functions of SPARC include inhibition of cell adhesion, inhibition of cell proliferation, and regulation of intercellular cement, for example (Bradshaw and Sage, J. Clin. Invest, 107: 1049-1054, 2001; and Brekken and Sage, Matrix Biol., 2001; 19: 816-827). SPARC regulates interaction between intercellular cement and cells through binding of structural proteins of such intercellular cements such as collagen.

In a human adult, SPARC is expressed at high levels in bone, blood platelets, wounded sites, or sites such as tumor sites where tissues are repeatedly reconstructed. There are many reports concerning the relationship between SPARC and tumors concerning various types of carcinoma. Tumor cells or host interstitial cells and inflammatory cells in tumor tissues express SPARC.

Ledda et al. have reported that SPARC expression in human melanoma correlates with tumor progress as determined by immunohistological tests (Ledda et al., J. Invest. Delmatol., 108, 210-214, 1997). Furthermore, Ledda et al. have reported that suppression of SPARC expression in human melanoma cells using a SPARC antisense expression vector results in in vitro disappearance of adhesion properties and infiltration properties and in vivo disappearance of carcinogenicity (Ledda et al., Nature Med., 3, 171-176, 1997).

DISCLOSURE OF THE INVENTION

Object to be Achieved by the Invention

Examples of tumor markers for melanoma include serum LDH, 5-S-cysteinyldopa (5-S-CD) that is broadly used in Japan, and S-100β protein and melanoma inhibitory activity (MIA) protein that have been reported as more sensitive markers in recent years. However, none of these tumor markers yield positive results unless the melanoma is at a highly advanced stage, such as Stage IV. Therefore, it must be said that the usefulness of these tumor markers is limited in terms of early diagnosis of and early detection of postoperative recurrence of melanoma. The object to be achieved by the present invention is to find out another tumor marker which is useful for early diagnosis of melanoma, and provide a diagnostic kit and diagnostic method for malignant melanoma using such marker.

Means to Achieve the Object

The present inventors previously detected a soluble GPC3 protein in the serum of hepatocellular carcinoma patients and melanoma patients, thus revealing that GPC3 can be a novel tumor marker for hepatocellular carcinoma and melanoma. Similar to the case of GPC3, the present inventors have detected a soluble SPARC protein in the serum and plasma of melanoma patients, thereby discovering that the SPARC protein can be a novel tumor marker for melanoma. Early melanoma could be detected by measuring the SPARC protein, as in the case of GPC3. The diagnostic yield could be increased to 60% by measuring the SPARC protein in combination with the measurement of GPC3.

The present invention provides the following (1) to (5):
(1) A diagnostic kit for malignant melanoma, which comprises an antibody against SPARC and an antibody against GPC3;
(2) A diagnostic method for malignant melanoma, wherein SPARC and GPC3 in a sample are measured;
(3) The diagnostic method according to (2), which comprises the steps of causing a sample to come into contact with an antibody against SPARC and causing the sample to come into contact with an antibody against GPC3;
(4) The diagnostic method according to (2) or (3), which comprising quantifying SPARC and GPC3 in a sample;
(5) The diagnostic method according to any one of (2) to (4), wherein the sample is serum or plasma.

PREFERRED EMBODIMENTS OF THE INVENTION

The present inventors have discovered that a combination of SPARC and GPC3 is a serum tumor marker that is useful for early diagnosis of melanoma with the use of the method described in Nakatsura, T. et al., Clin. Cancer Res. 10, 6612-6621, 2004.

The amino acid sequence of the human SPARC protein is known. For example, the amino acid sequence has been deposited with the GenBank protein database under accession No. NM 003118 and is easily obtained by persons skilled in the art.

The amino acid sequence of human GPC3 protein is known and can be easily obtained by persons skilled in the art.

The present invention provides a diagnostic kit for malignant melanoma which comprises an antibody against SPARC and an antibody against GPC3. The antibody against SPARC and the antibody against GPC3 that are used in the present invention may be either polyclonal or monoclonal antibodies and can be prepared by a method known by persons skilled in the art (e.g., see "New Biochemical Experiment 1 (Shin-Seikagaku Jikken Ko-za 1)," Protein I, pp. 389-406, TOKYO KAGAKU DOZIN CO., LTD.). The amino acid sequence of SPARC protein and that of the GPC3 protein are known as described above. These proteins can be produced based on such amino acid sequences using general protein expression techniques. Alternatively, commercially available proteins (Zymed Laboratories, CA) can also be used. Such commercially available SPARC or GPC3 is preferably used after the removal of SDS with the use of SDS-Out™ (Sodium Dodecyl Sulfate Precipitation Reagent; purchased from PIERCE, Rockford, Ill.), if necessary. Moreover, a partial peptide of SPARC or GPC3 can be produced by selecting an appropriate partial sequence from the amino acid sequence of SPARC or GPC3 and then using general peptide synthesis techniques.

To prepare a polyclonal antibody against SPARC or GPC3, an appropriate amount of the SPARC protein, the GPC3 protein, or a partial peptide thereof is administered to an animal such as a rabbit, a guinea pig, a mouse, or a fowl. Such protein or peptide may be administered together with an adjuvant (FIA or FCA) that promotes antibody production. Administration is generally performed every several weeks. Through a plurality of instances of immunization, the resulting antibody titer can be elevated. After final immunization, an anti-serum can be obtained by collecting blood from an immunized animal. The thus obtained anti-serum is subjected to fractionation by ammonium sulfate precipitation or anion chromatography, or affinity purification using protein A or an immobilized antigen, for example. Hence, a polyclonal antibody can be prepared.

In the meantime, a monoclonal antibody against SPARC or GPC3 can be prepared as follows. For example, an animal is immunized with the SPARC protein, the GPC3 protein, or a partial peptide thereof in a manner similar to that of the above description. After final immunization, the spleen or the lymph node is collected from the immunized animal. Antibody-producing cells contained in the spleen or the lymph node are fused to myeloma cells using polyethylene glycol or the like, thereby preparing hybridomas. A hybridoma of interest is screened for and then the hybridoma is cultured. The monoclonal antibody can be prepared from the culture supernatant. Such monoclonal antibody can be purified through fractionation by ammonium sulfate precipitation or anion chromatography, or through affinity purification using protein A or an immobilized antigen, for example. In addition, an antibody that is used for the purpose of the present invention may be an antibody that recognizes any epitope of SPARC or GPC3.

Furthermore, fragments of the above antibodies may also be used in the present invention. Examples of such antibody fragments include a F(ab')2 fragment and a Fab' fragment.

In view of the accuracy of a diagnostic agent, an antibody against SPARC and an antibody against GPC3 are preferably human type antibodies or human antibodies. A mouse-human chimeric antibody that is an example of such human type antibody can be prepared by isolating an antibody gene from mouse cells that produce an antibody against the SPARC protein or the GPC3 protein, recombining the H chain constant region with a human IgE H chain constant region gene, and then introducing the resultant into mouse myeloma cells. Furthermore, a human antibody can be prepared by immunizing a mouse (in which the immune system has been replaced by a human immune system) with the SPARC protein or the GPC3 protein.

For example, in the diagnostic kit of the present invention, an antibody against SPARC or an antibody against GPC3 can be used at a concentration of (but not limited to) 0.5 µg/ml. The diagnostic kit of the present invention may appropriately contain a pharmaceutically acceptable carrier or the like, if necessary, in addition to the above antibodies against SPARC and GPC3.

The present invention further provides a diagnostic method for malignant melanoma, which comprises measuring SPARC and GPC3 in a sample. For example, SPARC and GPC3 in a sample can be measured by the steps of causing the sample to come into contact with an antibody against SPARC and causing the sample to come into contact with an antibody against GPC3. Examples of a sample in the present invention include serum, saliva, and urine obtained from subjects who may be affected with melanoma. A particularly preferable sample is a serum sample, for example. A sample may be caused to come into contact with the above antibody based on a method that is generally performed in the art, and the method therefore is not particularly limited. For example, diagnosis can be made by causing a sample to come into contact with the above antibodies and then quantitatively detecting the specific binding between SPARC (that can be present in the sample) and the corresponding antibody and the specific binding between GPC3 (that can be present in the sample) and the corresponding antibody with the use of a fluorescent substance, a light-emitting substance, a secondary antibody labeled with an enzyme or the like. Reaction for diagnosis may also be performed in the liquid phase, such as in wells, or on solid-phase supports on which an antibody against SPARC or GPC3 has been immobilized. In this case, whether or not a measured value is melanoma-positive can be determined through comparison with a standard value that has been previously determined using normal samples not affected with melanoma or samples known to be affected with melanoma. Moreover, upon diagnosis, it is preferable to determine a cut-off value through measurement of serum SPARC and serum GPC3 levels in many melanoma patients and healthy subjects.

Specific examples of methods for immunologically detecting SPARC and GPC3 in a sample using an antibody against SPARC and an antibody against GPC3 include enzyme immunoassay (EIA) such as sandwich ELISA and radioimmunoassay (RIA). These techniques are known by persons skilled in the art. For example, in sandwich ELISA, 2 types of antibody having different antigen recognition sites are prepared and then one antibody type is adsorbed onto a plate in advance. A sample is caused to come into contact with the plate to perform a reaction. A reaction with the other antibody type having a different antigen recognition site and a reaction with an anti-immunoglobulin antibody labeled with an enzyme such as peroxidase or alkaline phosphatase are performed. A substrate that develops color because of the presence of such an enzyme is added to perform a color development reaction. The intensity of color developed is measured using a spectrophotometer. Hence, SPARC and GPC3 in the sample can be detected or measured. Furthermore, in radioimmunoassay, procedures similar to those used in the above form of enzyme immunoassay using an antibody not labeled with an enzyme but labeled with a radioactive material such as $^{125}I$ are undertaken, and then radiation is measured using a scintillation counter.

The diagnostic method of the present invention can be used for diagnosing whether or not a subject is affected with melanoma. Furthermore, the diagnostic method can also be performed over time so as to confirm therapeutic effects against melanoma.

The kit of the present invention contains at least the above antibody against SPARC and the above antibody against GPC3. Furthermore, the kit of the present invention can also appropriately contain reagents (e.g., a secondary antibody, a color reagent, and a buffer) required for detection of SPARC and GPC3 in a sample.

The present invention will be further described specifically by referring to examples. However, the present invention is not limited by these examples.

EXAMPLES

Example 1

SPARC mRNA Expression in Mouse Cell Lines

SPARC mRNA expression was examined by reverse transcriptase-PCR (RT-PCR). B16, B16F1, B16F10, EL4 MCA, and LLC mouse cell lines were obtained from the Cell Resource Center for Biomedical Research, Institute of Development, Aging and Cancer, Tohoku University.

RT-PCR was performed according to a known method (e.g., Nakatsura T. et al., Biochem. Biophys. Res. Commun. 281, 936-944 (2001)). Mouse SPARC gene-specific PCR primers capable of amplifying a 533-bp fragment were designed. RT-PCR reaction was performed using the primers, and it consisted of 5 minutes of initial denaturation at 94° C. followed by 30 amplification cycles at an annealing temperature of 58° C. The SPARC PCR primer sequences used herein were sense: 5'-GTCCCACACTGAGCTGGC-3' (SEQ ID NO: 1) and antisense: 5'-AAGCACAGAGTCTGGGT-GAGTG-3' (SEQ ID NO: 2).

The mouse cell lines were compared in terms of SPARC MRNA expression. FIG. 1A shows the results. In FIG. 1A, lane 1 indicates B16, lane 2 indicates B16-F1, lane 3 indicates B16-F10, lane 4 indicates MCA, lane 5 indicates NIH-3T3, lane 6 indicates LLC, and lane 7 indicates EL4.

As is understood from the results in FIG. 1A, B16, B16Fl, and B16F10 melanoma cell lines exhibited strong SPARC mRNA expression. Expression was also observed in MCA, LLC, and NIH/3T3, however, no such expression was observed in EL4 (FIG. 1A).

Example 2

SPARC mRNA Expression in Human Melanoma Cell Lines

SPARC mRNA expression was examined by reverse transcriptase-PCR (RT-PCR). G361, CRL1579, SK-MEL-28, and HMV-I melanoma cell lines were obtained from the Cell Resource Center for Biomedical Research, Institute of Development, Aging and Cancer, Tohoku University. 526mel and 888mel were donated by Dr. Y. Kawakami of Keio University. Moreover, 164, SK-MEL-19, HM3KO, MEWO, and colo38 were donated by Dr. T. Kageshita of Kumamoto University. Furthermore, normal human epidermal melanocytes, NHEM, were purchased from KURABO (KURABO INDUSTRIES LTD.).

RT-PCR was performed according to a known method (e.g., Nakatsura T. et al., Biochem. Biophys. Res. Commun. 281, 936-944 (2001)). Human SPARC gene-specific PCR primers capable of amplifying a 343-bp fragment were designed. RT-PCR reaction was performed using the primers, and it consisted of 5 minutes of initial denaturation at 94° C. followed by 26 amplification cycles at an annealing temperature of 58° C.

The SPARC PCR primer sequences used herein were sense: 5'-CGAAGAGGAGGTGGTGGCGGAAAA-3' (SEQ ID NO: 3) and antisense: 5'-GGTTGTTGTCCTCATC-CCTCTCATAC-3' (SEQ ID NO: 4). β-actin PCR primer sequences that were used for control experiments were sense: 5'-CCTCGCCTTTGCCGATCC-3' (SEQ ID NO: 5) and antisense: 5'-GGATCTTCATGAGGTAGTCAGTC-3' (SEQ ID NO: 6).

After standardization using a control β-actin mRNA, melanoma cell lines were compared in terms of SPARC mRNA expression. FIG. 1B shows the results. In FIG. 1B, lane 1 indicates 164, lane 2 indicates 888, lane 3 indicates HM3KO, lane 4 indicates CRL1579, lane 5 indicates 526mel, lane 6 indicates G361, lane 7 indicates MEWO, lane 8 indicates SK-MEL-28, lane 9 indicates SK-MEL-19, lane 10 indicates Colo38, lane 11 indicates HMV-I, and lane 12 indicates NHEM (melanocyte).

As is understood from the results in FIG. 1B, elevated expression was observed in 164, 888mel, HM3KO, CRL1579, 526mel, G361, MEWO, SK-MEL-28, SK-MEL-19, colo38, and NHEM, however, no such expression was observed in HMV-I. In addition, expression was also observed in normal melanocytes.

Example 3

SPARC Protein Expression in Human Melanoma Tissues

SPARC protein expression in normal human skin, human pigmented nevus tissues, and human melanoma tissues was examined by the Western blotting method. Specimens used herein were donated by Dr. T. Kageshita, for which informed consent had been obtained from donors treated at the Department of Dermatology, Kumamoto University School of Medicine.

Western blotting was performed by a known method. Samples were subjected to 7% acrylamide gel electrophoresis, transferred to nitrocellulose membranes (Bio Rad), and then blocked (4° C. overnight) using a 0.2% Tween20-TBS solution supplemented with 5% skim milk and 1% BSA. Incubation was performed for 1 hour at room temperature using as primary antibodies an anti-human HSP105 mouse monoclonal antibody (Haematologic Technologies, U.S.A.) and a control mouse monoclonal anti-human β-actin antibody (Sigma). After washing, incubation was performed for 30 minutes using an HRP-labeled anti-mouse antibody (Amersham Bioscience). After washing, detection was performed using ECL Western Blotting Detection Reagents (Amersham Bioscience).

FIG. 2 shows the results. In FIG. 2, lane 1 indicates nevi, lane 2 indicates patient 1 (acral lentiginous melanoma) with normal skin, lane 3 indicates patient 1 with patches, lane 4 indicates patient 1 with melanoma, lane 5 indicates patient 2 (acral lentiginous melanoma) with normal skin, lane 6 indicates patient 2 with patches, lane 7 indicates patient 2 with melanoma, lane 8 indicates patient 3 with melanoma (superficial spreading melanoma), lane 9 indicates patient 4 with normal skin (superficial spreading melanoma), lane 10 indicates patient 4 with patches (superficial spreading melanoma), lane 11: patient 4 with melanoma (superficial spreading melanoma), and lane 12 indicates patient 5 with melanoma (superficial spreading melanoma) metastasis.

As is understood from the results in FIG. 2, SPARC protein was expressed at extremely low levels in nevi, normal skin, and patches, and SPARC protein was expressed at high levels in all melanoma tissues.

Example 4

Presence of Soluble SPARC Protein in the Culture Supernatants of Melanoma Cell Lines and in the Serum of Melanoma Patients A 96-well ELISA plate (Nunc, Denmark) was coated with 0.05 μg/well anti-human SPARC monoclonal antibody (Zymed laboratories, San Francisco) in PBS (pH 7.4) at room temperature overnight. Subsequently, the plate was blocked using 100% Block Ace (Dainippon Pharmaceutical Co. Ltd.) at room temperature for 1 hour. A positive control standard sample, a culture supernatant, and the serum of a patient, which had been diluted 200-fold with 10% Block Ace, were added together with the biotinylated anti-human SPARC polyclonal antibody (R&D system, Minneapolis), followed by 2 hours of incubation at room temperature. After 3 times of washing with PBS, HRP-conjugated streptavidin (ENDOGEN, Woburn) was added to each well. After 30 minutes of incubation, the plate was washed 3 times with PBS, and a TMB substrate solution (ENDOGEN) was added. An ELISA reader (model 550, Bio-Rad) was used at 450 nm for analysis.

After obtainment of informed consent, serum samples were obtained from melanoma patients treated at the Department of Dermatology, Kumamoto University School of Medicine. SPARC is a secretory protein, as is indicated by the name. The present inventors attempted to detect if the SPARC protein is also secreted in melanoma.

Detection was performed by Enzyme-Linked Immunosorbent Assay (ELISA) using an anti-human SPARC antibody and a biotinylated anti-human SPARC polyclonal antibody. With the use of a commercially available SPARC protein (Haematologic Technologies, U.S.A.), the accuracy of SPARC determination in the ELISA system was confirmed. A standard curve for quantitative detection of the SPARC protein was evaluated based on OD data using the serial dilution of the SPARC protein. The SPARC protein was detected in the culture supernatants of 10 out of 11 types of melanoma cell lines (FIG. 3).

Next, the soluble SPARC protein in the serum of melanoma patients was detected. Blood samples were collected from 87 preoperative melanoma patients. The patients' profiles were collected from the medical records and then clinical stages were determined based on the TNM classification. SPARC protein levels in the serum of 87 melanoma patients and 60 healthy donors (HD) were evaluated by ELISA (FIGS. 4 and 5). The SPARC protein thought to be derived from blood platelets was also detected in HD serum. Even higher SPARC protein levels were detected in some of the melanoma patients. When the mean value+2SD (2337 ng/ml) of HD was determined to be a cut-off value, 29 (33.3%) out of 87 melanoma patients were found to be positive, but 3 out of 60 healthy subjects were found to be positive, and the degree of specificity was 95%. Furthermore, in the serum of 7 out of 10 cases; that is, 7 out of 10 melanoma patients who had exhibited preoperative positive values and for which postoperative follow-up had been successfully performed, the SPARC protein was undetected in the serum after excision. The SPARC protein thought to be derived from blood platelets was also detected in the serum of healthy subjects. Hence, to exclude the effects of platelet-derived SPARC protein, SPARC protein levels in the plasma of 11 melanoma patients and 21 healthy donors (HDs) were evaluated by ELISA (FIG. 6). When 500 ng/ml SPARC protein was determined to be a cut-off value, the mean value for melanoma patients was 606 ng/ml, 4 (36.4%) out of 11 melanoma patients were found to be positive, the mean value for healthy subjects was 140 ng/ml, 1 out of 21 healthy subjects was found to be positive, and the degree of specificity was 95%.

Furthermore, soluble MIA, 5-S-CD, GPC3, SPARC, and SPARC or GPC3 were detected in the serum of melanoma patients. Table 1 shows the results. Similar to the case of GPC3, SPARC was also found to be effective in diagnosis of melanoma even at early stages including stages I and II. Moreover, 60 percent or more of melanoma patients could be screened for with the use of SPARC and GPC3. Furthermore, percentages of patients for whom positive results for both SPARC and GPC3 were gained from the same serum samples are as shown in the following Table 2.

TABLE 1

| stage | MIA | 5-S-CD | GPC3 | SPARC | GPC3 + SPARC |
| --- | --- | --- | --- | --- | --- |
| 0 | 1/9 (11.1%) | 0/9 (0.0%) | 4/9 (44.4%) | 5/9 (55.5%) | 8/9 (88.9%) |
| I | 5/25 (20.0%) | 2/25 (8.0%) | 10/25 (40.0%) | 3/23 (13.0%) | 11/24 (48.0%) |
| II | 1/21 (4.8%) | 2/20 (10.0%) | 10/21 (47.6%) | 5/19 (26.3%) | 15/21 (71.4%) |

TABLE 1-continued

| stage | MIA | 5-S-CD | GPC3 | SPARC | GPC3 + SPARC |
|---|---|---|---|---|---|
| III | 3/18 (16.7%) | 5/18 (27.8%) | 7/18 (38.9%) | 8/18 (44.4%) | 12/18 (66.7%) |
| IV | 9/18 (50.0%) | 15/18 (83.3%) | 5/18 (27.8%) | 8/18 (44.4%) | 11/18 (61.1%) |
| Total | 19/91 (20.9%) | 24/90 (26.7%) | 36/91 (39.6%) | 29/87 (33.3%) | 57/90 (63.3%) |

TABLE 2:

| Stage | Positive for GPC only | Positive for SPARC only | Positive for both GPC and SPARC | Positive for GPC or SPARC |
|---|---|---|---|---|
| 0 | 3/9 | 4/9 | 1/9 | 8/9 |
| I | 9/25 | 2/23 | 1/23 | 12/23 |
| II | 10/21 | 5/19 | 0/19 | 15/19 |
| III | 4/18 | 5/18 | 3/18 | 12/18 |
| IV | 3/18 | 6/18 | 2/18 | 11/18 |
| Total | 29/91 | 22/87 | 7/87 | 58/87 |

As is clear from the results shown in Tables 1 and 2 and FIG. 5, a conventional tumor (melanoma) marker, 5-S-CD, and the recent subject of attention MIA were both useful only for advanced melanoma cases at stage III or IV. Similar to the case of GPC3, SPARC was effective in diagnosis of melanoma even at early stages I and II. However, few cases were positive for both SPARC and GPC3. SPARC is thought to be secreted in serum by an individual mechanism. Diagnostic yield can be elevated with the combined use of SPARC and GPC3. Specifically, it was revealed that the use of SPARC and GPC3 in combination enables screening of 60 percent or more of melanoma patients and that this combination is useful as a novel tumor marker for melanoma. A MIA ELISA kit (Roche Germany) was used for measurement of MIA.

Furthermore, the soluble SPARC protein in the serum of melanoma patients was detected, and the patients were classified via visual melanoma classification. Table 3 shows the results. Increased SPARC protein levels were observed in various tissue types, regardless of differences in melanoma tissue types.

TABLE 3

| Type | Positive for GPC only | Positive for SPARC only | Positive for both GPC and SPARC | Positive for GPC or SPARC |
|---|---|---|---|---|
| ALM | 11/44 | 9/41 | 4/41 | 24/41 |
| SSM | 7/16 | 5/16 | 1/16 | 13/16 |
| LMM/LM | 4/9 | 4/8 | 0/8 | 8/8 |
| NM | 1/5 | 0/5 | 1/5 | 2/5 |
| Mucosa | 4/12 | 4/12 | 0/12 | 8/12 |
| Total | 27/86 | 22/82 | 6/82 | 55/82 |

The results in Table 3 suggest that the use of SPARC and GPC can contribute to diagnosis of various tissue types, regardless of differences among tissue types such as in the cases of acral lentiginous melanoma, which occurs on the soles of feet and is frequently found in Japanese people, superficial spreading melanoma and lentigo maligna melanoma, which are frequently found in Western people.

Table 4 shown below lists changes in serum SPARC levels (unit: ng/ml) in 16 melanoma patients before and after operation. In 13 out of 16 cases, serum SPARC levels decreased to the cut-off value (2340 ng/ml) or lower after operation.

TABLE 4

| Patient | |
|---|---|
| Stage 0 | |
| No. 1 | Before operation (4699 ng/ml), and 566 days after operation (1555 ng/ml) |
| No. 2 | Before operation (3183 ng/ml), and 7 days after operation (2303 ng/ml) |
| No. 3 | Before operation (3011 ng/ml), and 15 days after operation (3441 ng/ml) |
| No. 4 | Before operation (2530 ng/ml), and 1484 days after operation (513 ng/ml) |
| No. 5 | Before operation (3046 ng/ml), and 37 days after operation (3246 ng/ml) |
| Stage IA | |
| No. 6 | Before operation (3278 ng/ml), and 274 days after operation (858 ng/ml) |
| Stage IB | |
| No. 7 | Before operation (2847 ng/ml) and 1581 days after operation (1366 ng/ml) |
| No. 8 | Before operation (3356 ng/ml), 140 days after operation (1969 ng/ml), and 217 days after operation (2330 ng/ml) |
| Stage IIA | |
| No. 9 | Before operation (2884 ng/ml), and 1472 days after operation (1555 ng/ml) |
| No. 10 | Before operation (3896 ng/ml), 1008 days after operation (3348 ng/ml), and 1358 days after operation (2624 ng/ml) |
| Stage IIB | |
| No. 11 | Before operation (3812 ng/ml), and 1567 days after operation (2275 ng/ml) |
| No. 12 | Before operation (2570 ng/ml), and 154 days after operation (1331 ng/ml) |
| Stage IIC | |
| No. 13 | Before operation (4152 ng/ml), 329 days after operation (2027 ng/ml), 437 days after operation (1052 ng/ml), 462 days after operation (1574 ng/ml), and 632 days after operation (801 ng/ml) |

TABLE 4-continued

| Patient | |
|---|---|
| Stage IIIA | |
| No. 14 | Before operation (2391 ng/ml) and 571 days after operation (1760 ng/ml) |
| Stage IIIB | |
| No. 15 | Before operation (3245 ng/ml), 82 days after operation (2414 ng/ml), 345 days after operation (1426 ng/ml), and 713 days after operation (3509 ng/ml) |
| Stage IIIC | |
| No. 16 | Before operation (3864 ng/ml), 465 days after operation (340 ng/ml), 678 days after operation (2380 ng/ml), and 762 days after operation (2184 ng/ml) |

INDUSTRIAL APPLICABILITY

The diagnostic kit and the diagnostic method according to the present invention are very useful in diagnosing whether or not a subject is affected with melanoma. It was revealed that the combination of SPARC and GPC3 is very useful in applications pertaining to cancer diagnosis for many melanoma patients throughout the world.

Figure 1:
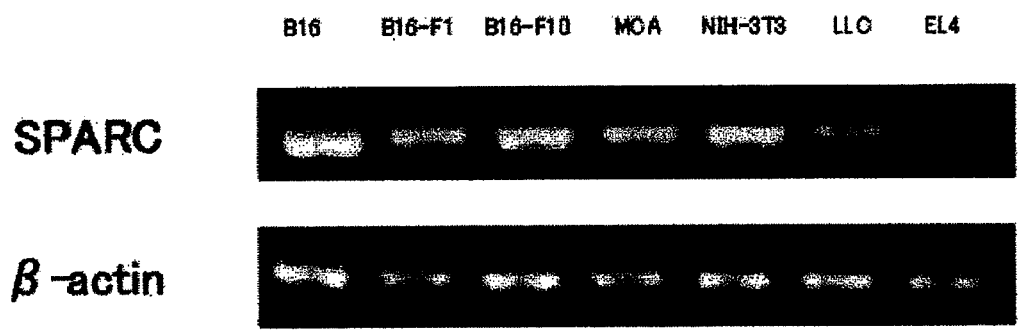
FIG. 1 shows SPARC mRNA expression.
Figure 1:
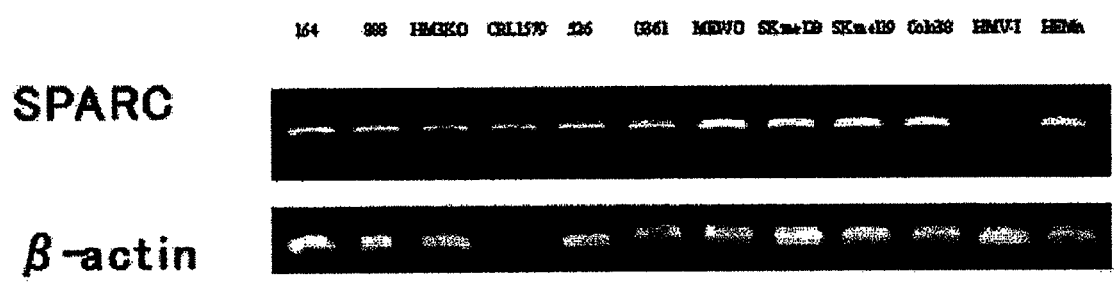
Figure 2:
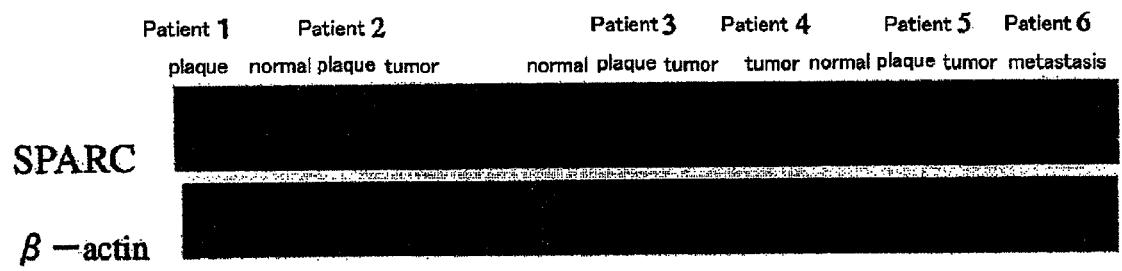
FIG. 2 shows SPARC protein expression in human melanoma tissue as determined by the Western blotting method.
Figure 3:
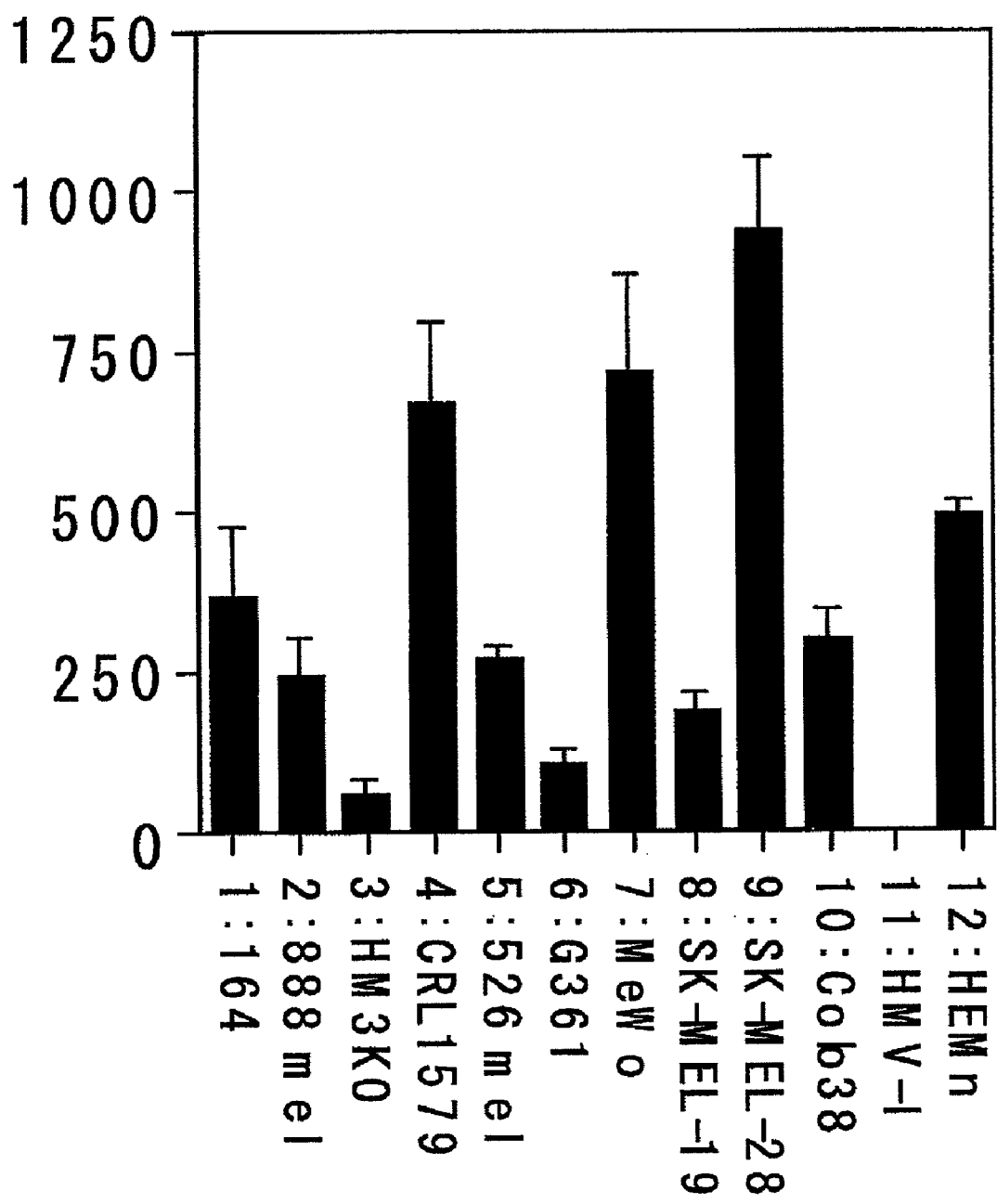
FIG. 3 shows the levels of GPC3 protein secreted in the culture supernatants of melanoma cell lines as determined by ELISA.
Figure 4:
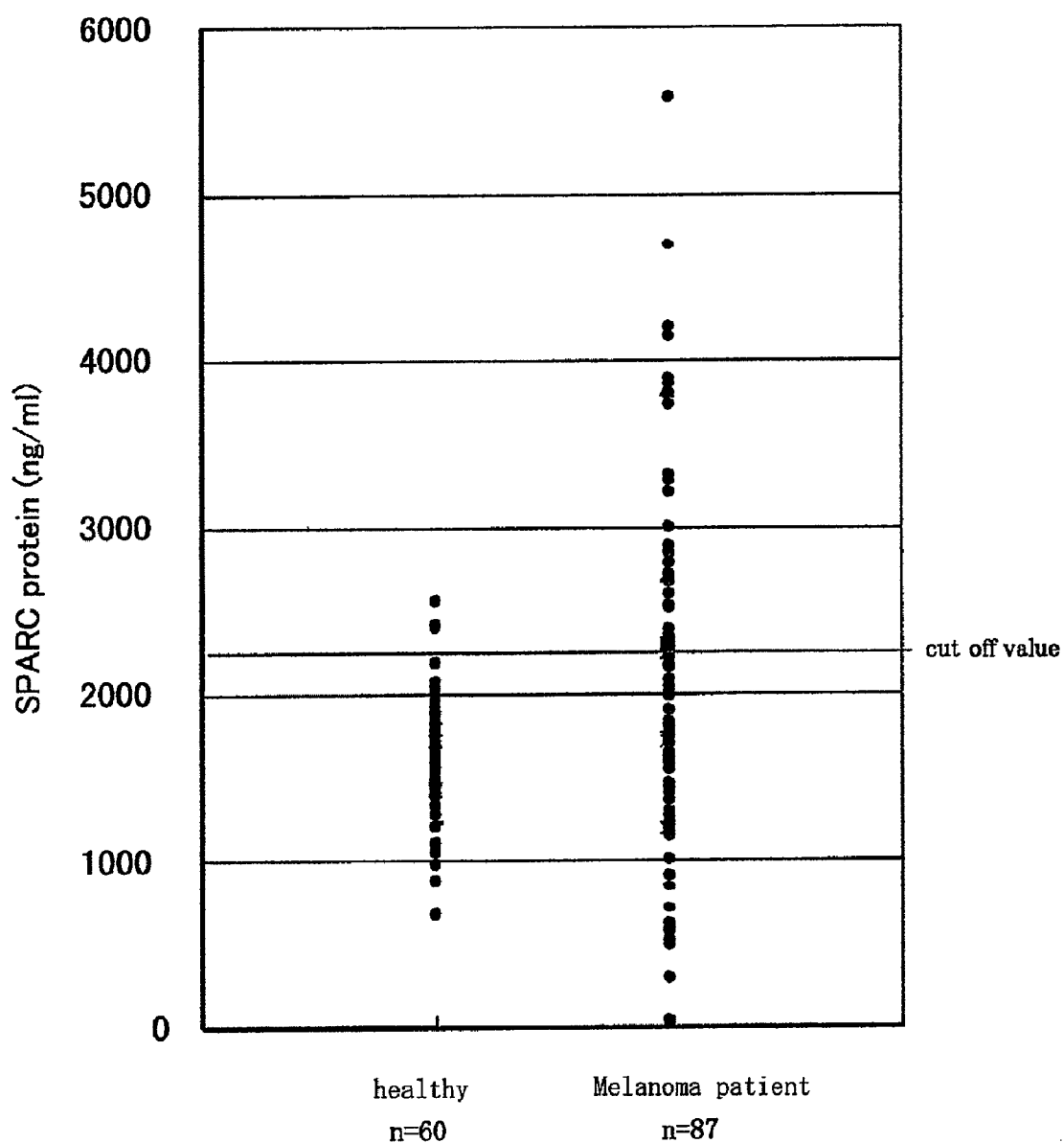
FIG. 4 shows the presence of the soluble SPARC protein in the serum of melanoma patients.
Figure 5:
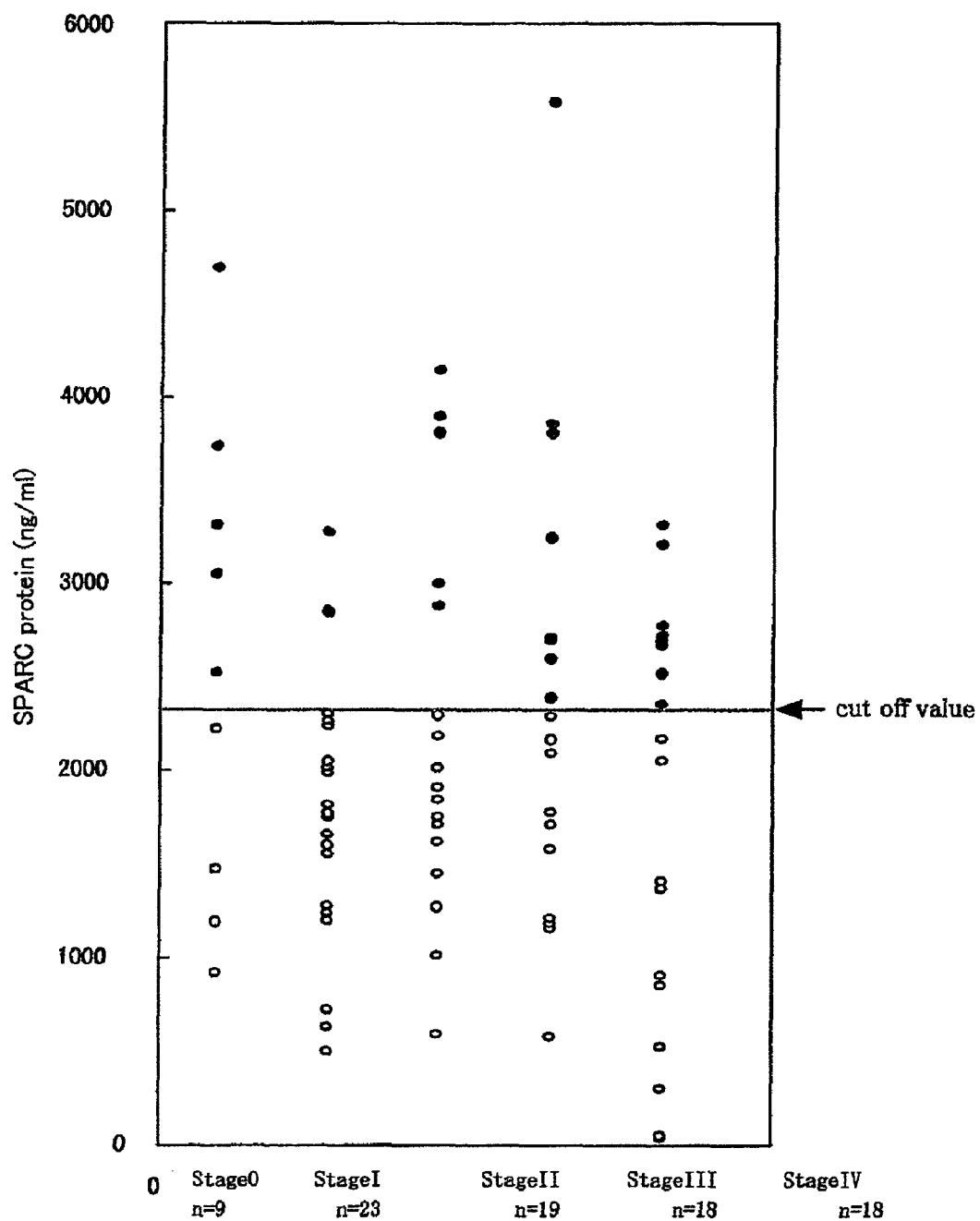
FIG. 5 shows the presence of the soluble SPARC protein in the serum of melanoma patients at each stage.
Figure 6:
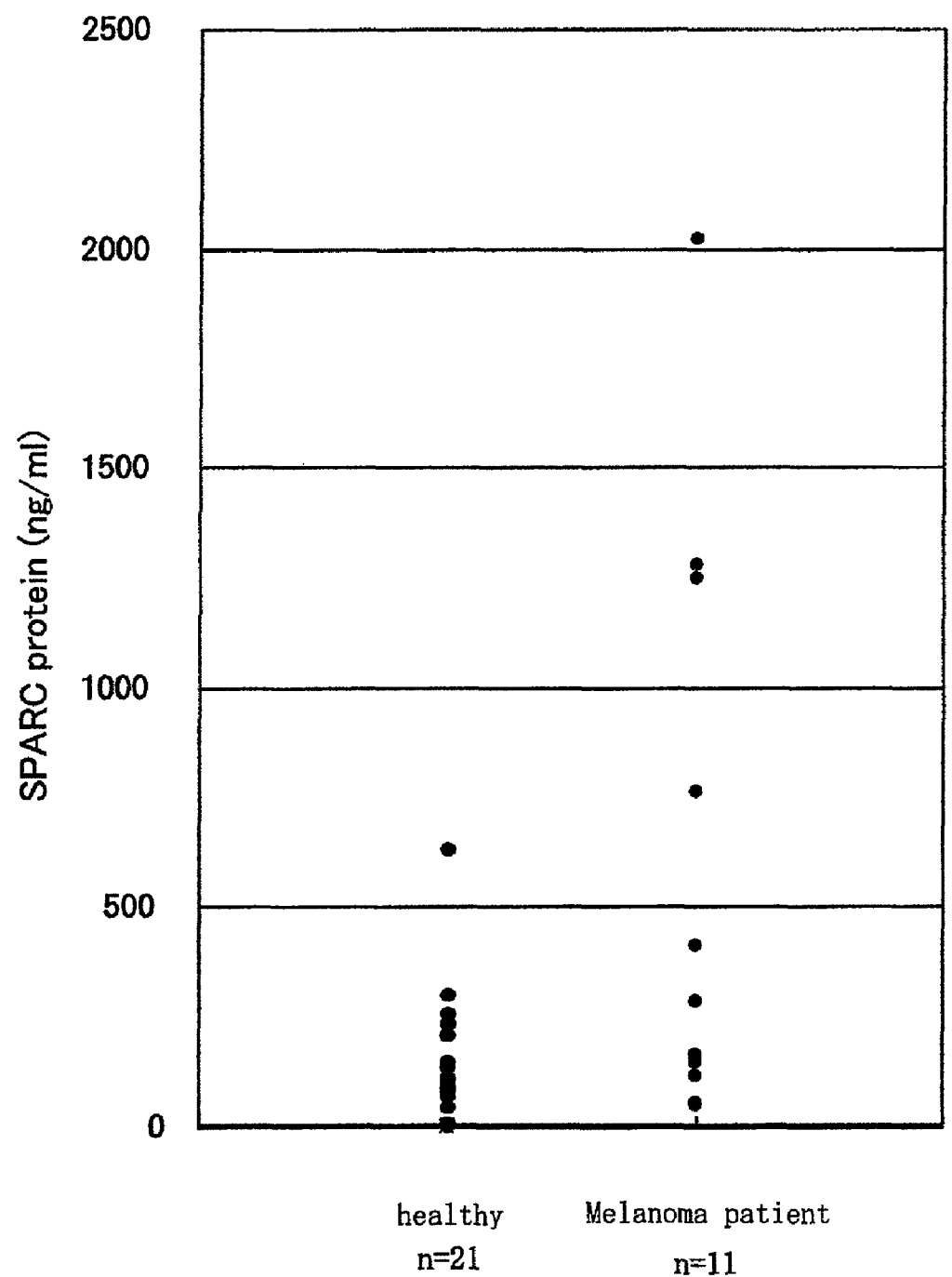
FIG. 6 shows the presence of the soluble SPARC protein in the plasma of melanoma patients.

The invention claimed is:

1. A diagnostic kit for detecting malignant melanoma, which comprises an antibody against secreted protein, acidic, rich in cysteine (SPARC) and an antibody against glypican-3 (GPC3).

2. A diagnostic method for detecting malignant melanoma, which comprises measuring SPARC and GPC3 in a sample.

3. The diagnostic method according to claim 2, which comprises causing a sample to come into contact with an antibody against SPARC and causing the sample to come into contact with an antibody against GPC3.

4. The diagnostic method according to claim 2, which comprises quantifying SPARC and GPC3 in a sample.

5. The diagnostic method according to claim 2, wherein the sample is serum or plasma.

* * * * *

```
                        SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtcccacact gagctggc                                                   18

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagcacagag tctgggtgag tg                                              22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgaagaggag gtggtggcgg aaaa                                            24

<210> SEQ ID NO 4
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggttgttgtc ctcatccctc tcatac                                          26

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctcgccttt gccgatcc                                                   18

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatcttcat gaggtagtca gtc                                             23
```